(12) United States Patent
McCoy

(10) Patent No.: US 10,226,373 B1
(45) Date of Patent: Mar. 12, 2019

(54) KNEE BRACE WITH ENHANCED SUPPORT AND SHOCK ABSORPTION ADJUSTABILITY

(71) Applicant: Daniel K McCoy, Upland, CA (US)

(72) Inventor: Daniel K McCoy, Upland, CA (US)

( * ) Notice: Subject to any disclaimer, the term of this patent is extended or adjusted under 35 U.S.C. 154(b) by 516 days.

(21) Appl. No.: 15/048,368

(22) Filed: Feb. 19, 2016

Related U.S. Application Data

(60) Provisional application No. 62/097,512, filed on Dec. 29, 2014.

(51) Int. Cl.
*A61F 5/01* (2006.01)

(52) U.S. Cl.
CPC .... *A61F 5/0125* (2013.01); *A61F 2005/0137* (2013.01); *A61F 2005/0197* (2013.01)

(58) Field of Classification Search
CPC ........ A61F 5/0102; A61F 5/012–5/013; A61F 2005/0132–2005/0158; A61F 2005/0165–2005/0179; A61F 2005/0197; F16H 63/38; G05G 5/06; G05G 5/08; G05G 5/12; G05G 5/14
USPC ................ 602/16; 70/312, 314; 74/526, 527
See application file for complete search history.

(56) References Cited

U.S. PATENT DOCUMENTS

| | | | | |
|---|---|---|---|---|
| 3,459,016 A | * | 8/1969 | Atkinson | E05B 37/02 70/312 |
| 3,768,333 A | * | 10/1973 | Bidwell | G05G 5/06 200/325 |
| 4,433,679 A | * | 2/1984 | Mauldin | A61F 5/0125 602/16 |
| 5,052,379 A | * | 10/1991 | Airy | A61F 5/0125 482/112 |
| 5,473,961 A | * | 12/1995 | Jackson | B05B 3/0431 116/307 |
| 5,658,241 A | * | 8/1997 | Deharde | A61F 5/0123 602/23 |
| 5,954,677 A | * | 9/1999 | Albrecht | A61F 5/0125 602/16 |
| 6,039,707 A | * | 3/2000 | Crawford | A61F 5/0193 602/18 |
| 6,056,712 A | * | 5/2000 | Grim | A61F 5/0127 602/16 |

(Continued)

OTHER PUBLICATIONS

A. https://web.archive.org/web/20141228204102/http://springloadedtechnology.com/products/series-knee-braces/.

*Primary Examiner* — Alireza Nia
*Assistant Examiner* — Lindsay A Jeffries
(74) *Attorney, Agent, or Firm* — Plager Schack LLP; Mark H. Plager; Eric Liou

(57) ABSTRACT

A knee brace worn by a user includes an upper frame assembly having a first pair of arms coupled together by an upper strap that encircles the user's thigh, each arm in the first pair of arms having an upper housing, a lower frame assembly having a second pair of arms coupled together by a lower strap that encircles a leg portion of the user, each arm in the second pair of arms having a lower housing pivotably mounted to one of the pair of upper housings of the first pair of arms, and a pair of spring assemblies connected to the brace. Each spring assembly is disposed within one of the upper housings and one of the lower housings, and includes a torsion spring that adjusts to one of a plurality of positions to permit the spring to store mechanical energy at a desired level.

8 Claims, 4 Drawing Sheets

(56) References Cited

U.S. PATENT DOCUMENTS

| | | | | |
|---|---|---|---|---|
| 6,471,664 B1* | 10/2002 | Campbell | ............. | A61F 5/0123 |
| | | | | 602/16 |
| 9,314,391 B2* | 4/2016 | Pittaccio | ................ | A61H 1/024 |
| 2006/0116616 A1* | 6/2006 | Albrecht | ............... | A61F 5/0125 |
| | | | | 602/23 |
| 2006/0260430 A1* | 11/2006 | Gard | ....................... | F16C 11/10 |
| | | | | 74/527 |
| 2007/0270976 A1* | 11/2007 | DeHarde | ............... | A61F 5/0125 |
| | | | | 623/27 |
| 2016/0374844 A1* | 12/2016 | DeHarde | ................ | F16F 15/04 |
| | | | | 602/16 |

* cited by examiner

KNEE BRACE WITH ENHANCED SUPPORT AND SHOCK ABSORPTION ADJUSTABILITY

RELATED APPLICATION

The application claims priority to provisional patent application U.S. Ser. No. 62/097,512 filed on Dec. 29, 2014, the entire contents of which is herein incorporated by reference.

BACKGROUND

The embodiments herein relate generally to knee braces.

Individuals with knee problems often experience pain. This limits their ability to perform daily activities such as walking, running or other physical activities. There exists a variety of knee braces that are used to provide a user with additional support to the knee region. In particular, several existing knee braces provide knee and/or leg support to individuals with existing injuries who perform activities such as standing and/or walking. Alternative existing knee braces provide additional support to individuals such as athletes engaging in higher leg impact activities such as running, jumping, or the like. However, these braces are limited in adjustability because they provide knee and/or leg support to individuals engaging in one particular class of activities such as minimal impact activities or high impact activities. These braces cannot be adjusted to effectively satisfy the support requirements for individuals engaging in both minimal impact activities and high impact activities.

As such, there is a need in the industry for a knee brace with enhanced support and shock absorption, which improves upon the prior art. Specifically, there is a need for a knee brace that adjusts to conform to the user's torsion requirements, which enhances flexibility of the brace in providing the requisite level of shock absorption to support the user when engaging in a wide range of activities.

SUMMARY

A knee brace configured to be worn by a user with enhanced support and shock absorption capabilities is provided. The knee brace comprises an adjustment mechanism to permit the user to configure the brace with enhanced flexibility to conform to torsion requirements of the user. The knee brace comprises an upper frame assembly detachably coupled to the user and comprising a first pair of arms, the first pair of arms coupled together by at least one upper adjustable strap configured to encircle a thigh portion of the user, each arm in the first pair of arms comprising an upper housing member, a lower frame assembly detachably coupled to the user and comprising a second pair of arms, the second pair of arms coupled together by at least one lower adjustable strap configured to encircle a leg portion of the user, each arm in the second pair of arms comprising a lower housing member pivotably mounted to one of the pair of upper housing members of the first pair of arms, and a pair of spring assemblies operably connected to the upper and lower frame assemblies, each spring assembly in the pair of spring assemblies disposed within one of the pair of upper housing members and one of the pair of lower housing members, each spring assembly comprising a torsion spring configured to be adjusted to one of a plurality of positions to permit the torsion spring to store mechanical energy at a desired level, thereby enabling the upper and lower frame assemblies to provide support to the user according to the torsion requirements.

BRIEF DESCRIPTION OF THE FIGURES

The detailed description of some embodiments of the invention will be made below with reference to the accompanying figures, wherein the figures disclose one or more embodiments of the present invention.

DETAILED DESCRIPTION OF CERTAIN EMBODIMENTS

Figure 1:
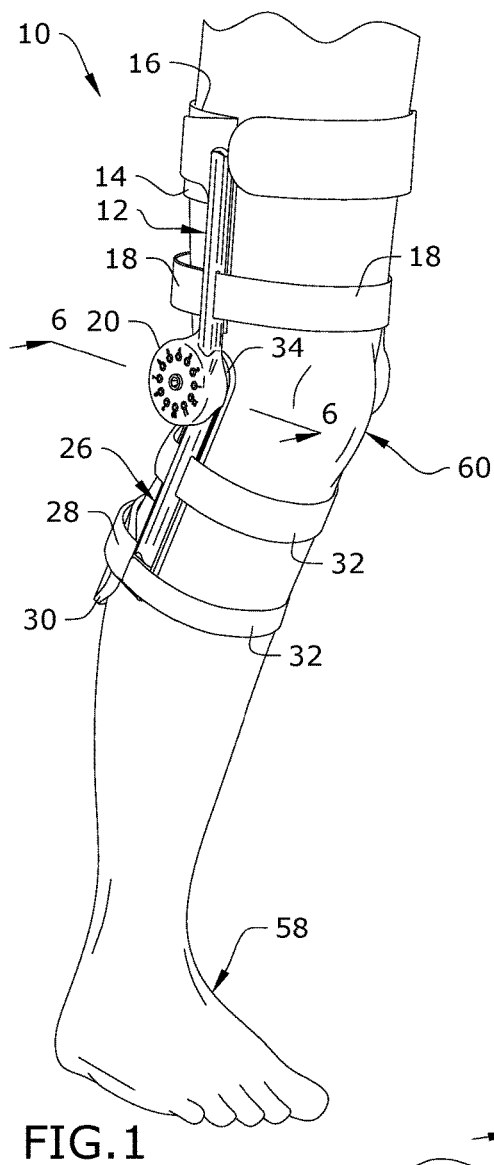
FIG. 1 depicts a perspective view of certain embodiments of the knee brace shown in use.
Figure 2:
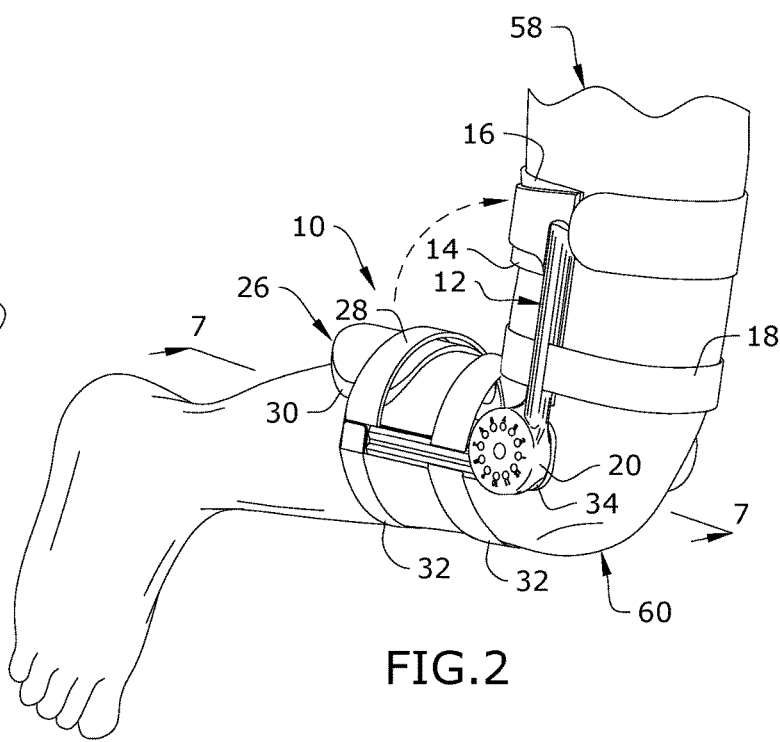
FIG. 2 depicts a perspective view of certain embodiments of the knee brace shown in use.

As depicted in FIGS. 1-2, knee brace 10 is configured to be secured around knee 60 of operator 58 to provide support and/or shock absorption according to the operator's torsion requirements. Knee brace 10 is configured to adjust to one of a plurality of adjustment settings to provide the requisite level of shock absorption to support the operator's knees and/or legs when performing a wide variety of activities including, but not limited to, standing, walking, basketball, football, cycling, tennis, motor sports, baseball or other sports. Knee brace 10 generally comprises an upper frame assembly pivotably mounted to a lower frame assembly to permit knee 60 of operator 58 to flex.

Figure 3:
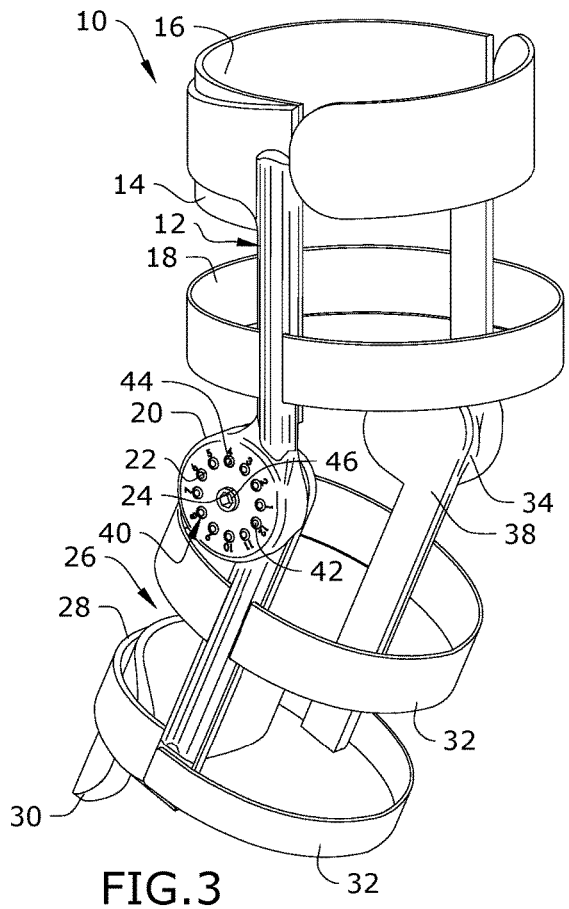
FIG. 3 depicts a perspective view of certain embodiments of the knee brace.
Figure 5:
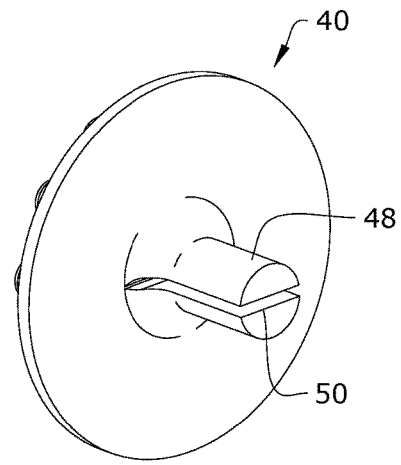
FIG. 5 depicts a perspective view of certain embodiments of the knee brace.
Figure 4:
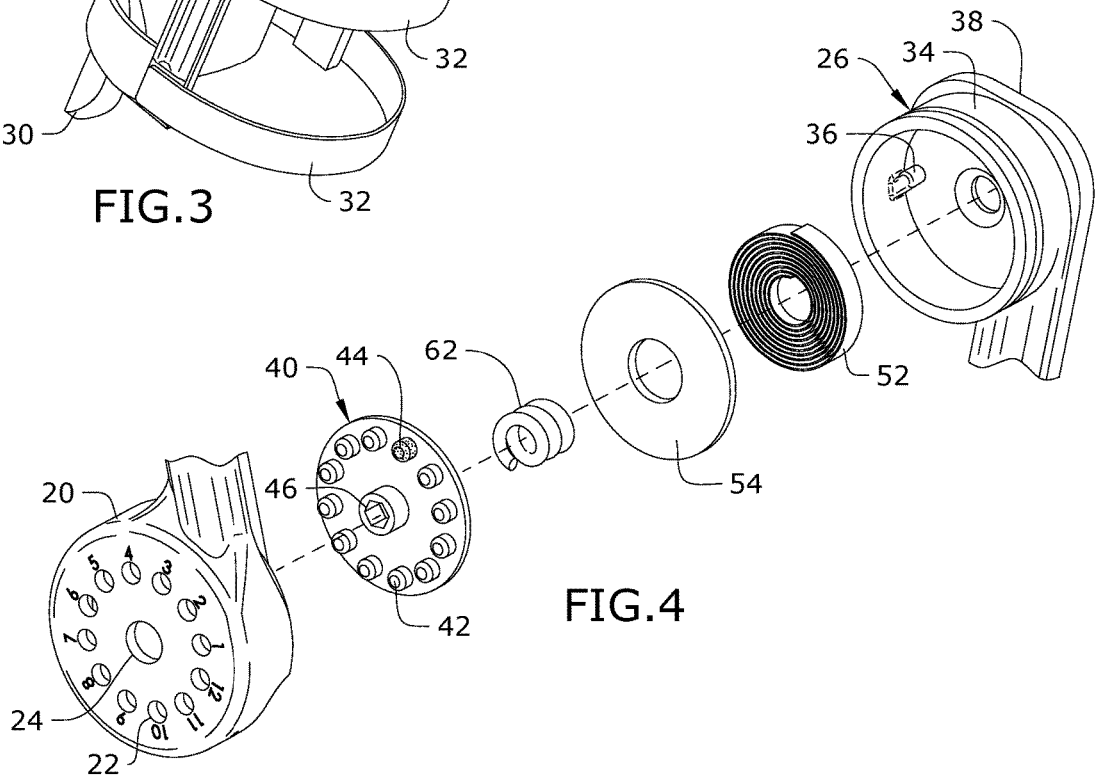
FIG. 4 depicts an exploded view of certain embodiments of the knee brace.

As depicted in FIGS. 3-5, the upper frame assembly of knee brace 10 comprises upper brace 12, which comprises a pair of arms and upper strap 18, upper rear arch 14 and upper rear arch padding 16 coupled thereto. Each arm of upper brace 12 comprises upper brace housing 20. Similarly, the lower frame assembly of knee brace 10 comprises lower brace 26, which comprises a pair of arms and lower straps 32, lower rear arch 28 and lower rear arch padding 30 coupled thereto. Each arm of lower brace 26 comprises lower brace housing 34. The pair of upper brace housings 20 is pivotably mounted to the pair of lower brace housings 34.

Components of upper brace 12 and lower brace 26 such as the arms, upper rear arch 14 and lower rear arch 28 may be made from materials such as plastic, carbon fiber, metals or other materials. Upper strap 18 and upper rear arch 14 are configured to encircle a thigh portion of operator 58. Lower straps 32 and lower rear arch 28 are configured to encircle a leg portion of operator 58. In one embodiment, upper strap 18 and lower straps 32 each comprises hook and loop fasteners to tightly secure the strap around operator 58. However, alternative fasteners may be used including snap fasteners, buckle components, zippers, or the like. It shall be appreciated that any alternative number of straps may be used on either the upper or lower frame assemblies of knee brace 10. In one embodiment, the interior face of each arm of upper brace 12 and lower brace 26 comprises a cushion member 38 affixed thereto, which preferably is a foam plate. Cushion member 38 provides a soft surface that contacts operator 58 to minimize skin abrasions and/or irritations when knee brace 10 is in use.

As depicted in FIGS. 4-5, a spring assembly is disposed within each upper brace housing 20 and a corresponding lower brace housing 34. Each spring assembly comprises lock pate 40, push spring 62, spring plate 54 and torsion spring 52. Lock plate 40 is preferably made from aluminum and comprises lock plate protrusions 42 and lock plate hex fitting 46 on a front side, and lock plate rear protrusion 48 and slot 50 on a rear side. Lock plate protrusions 42 are disposed along a circular pathway. Upper brace housing 20 comprises a plurality of lock holes 22 disposed along a circular pathway and center hole 24. This configuration permits center hole 24 of upper brace housing 20 to receive hex fitting 46 of lock plate 40. Similarly, lock holes 22 of upper brace housing 20 are configured to receive lock plate protrusions 42 on lock plate 40.

In one embodiment, one of lock plate protrusions 42 comprises a marking that designates lock plate indicator protrusion 44. Lock plate indicator protrusion 44 serves as a visual marker that illuminates the current spring torsion adjustment setting of knee brace 10. In a preferred embodiment, there exist twelve lock holes 22 on upper brace housing 20 and twelve corresponding lock plate protrusions 42 on lock plate 40. However, any alternative number of lock holes 22 and lock plate protrusions 42 may be used instead.

Push spring 62 preferably is made from plastic or metal, and comprises a first end in contact with lock plate 40 and a second end in contact with spring plate 54. More specifically, push spring 62 is configured to be disposed around lock plate rear protrusion 48. In alternative embodiments, it shall be appreciated that push spring 62 may be replaced by other types of spring mechanisms. Spring plate 54 is preferably made from plastic or metal and comprises a central opening configured to permit an intermediate portion of torsion spring 52 to pass therethrough (not shown).

Torsion spring 52 is preferably a 301 stainless steel coiled spring having an approximate width of 0.187 inches, length of 11.23 inches and thickness of 0.03 inches. However, the width of torsion spring 52 may vary within the approximate range of 0.175-0.2 inches. Torsion spring 52 comprises a first end inserted through the central opening of spring plate 54. This permits the first end of torsion spring 52 to be secured within slot 50 of lock plate 40. The second end of torsion spring 52 is coupled to torsion spring stop 36 of lower brace housing 34. Torsion spring stop 36 may be any receiving member and/or fastener such as a slot, pin, or the like.

Figure 6:
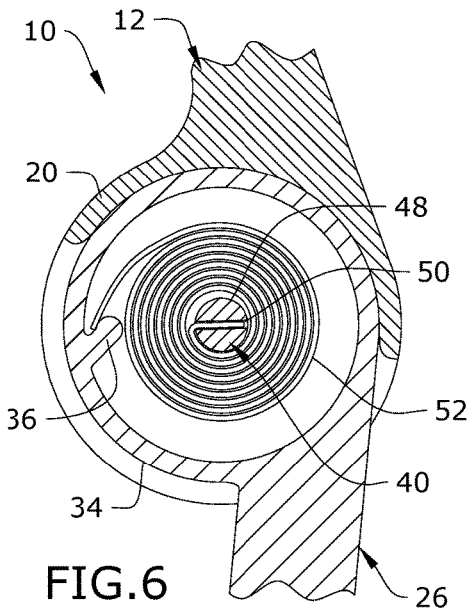
FIG. 6 depicts a section view of certain embodiments of the knee brace taken along line 6-6 in FIG. 1.
Figure 7:
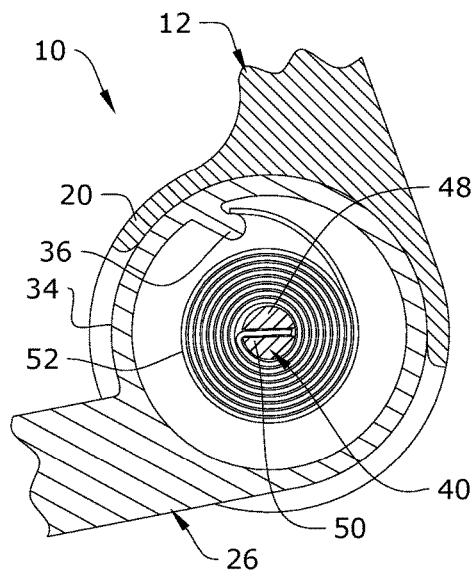
FIG. 7 depicts a section view of certain embodiments of the knee brace taken along line 7-7 in FIG. 2.

FIG. 6 depicts the spring assembly in the assembled configuration with torsion spring 52 coupled to slot 50 of lock plate 40 and torsion spring stop 36 of lower brace housing 34. FIG. 7 depicts the spring assembly in a flexed configuration when in use.

In operation, knee brace 10 is secured around knee 60 of operator 58 as shown in FIG. 1. Upper strap 18 and lower straps 32 are adjusted to secure knee brace 10 in place on operator 58. Although the figures depict a single knee brace, it shall be appreciated that a pair of knee braces 10 are preferably used, one secured to each leg of operator 58. Each knee brace 10 is adjusted to conform to the operator's torsion requirements based on the type of activity operator 58 engages in.

Figure 8:
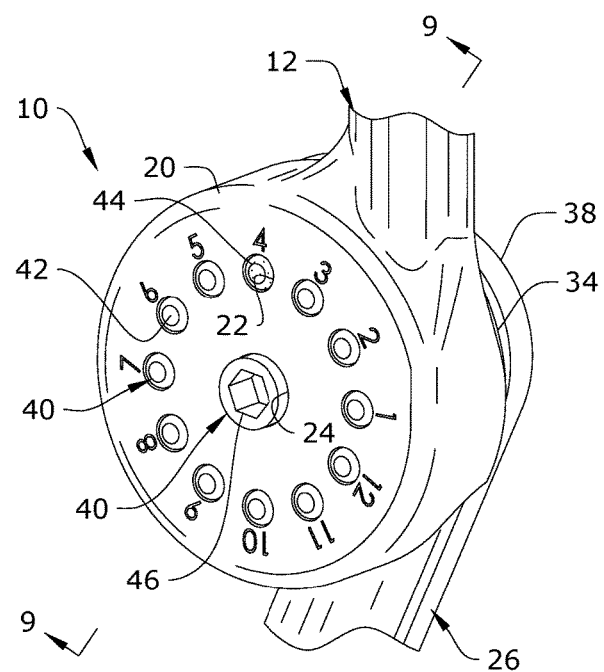
FIG. 8 depicts a perspective view of certain embodiments of the knee brace.
Figure 9:
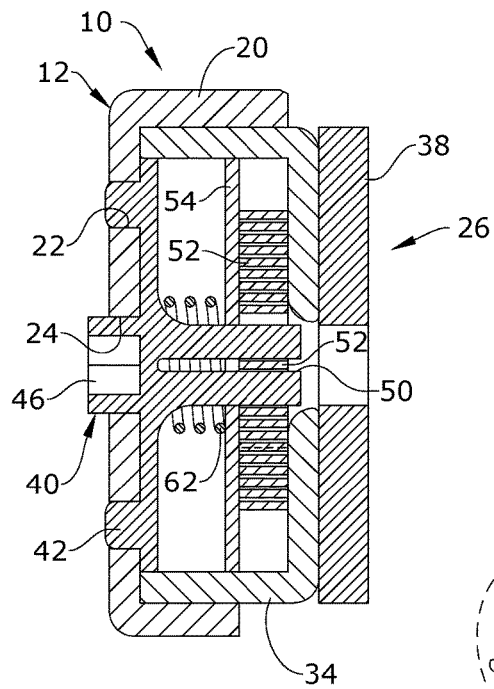
FIG. 9 depicts a section view of certain embodiments of the knee brace taken along line 9-9 in FIG. 8.

FIGS. 8-9 depict knee brace 10 with the spring assembly in a particular torsion setting. In this exemplary configuration, push spring 62 is in an extended state in contact with lock plate 40 and spring plate 54. This enables push spring 62 to apply a force against lock plate 40 to enable lock plate protrusions 42 to extend through lock holes 22 of upper brace housing 20. Similarly, lock plate hex fitting 46 extends through center hole 24 of upper brace housing 20. In this exemplary configuration, lock plate indicator protrusion 44 is disposed through adjustment setting four of the twelve adjustment settings denoted by the twelve lock holes 22.

Figure 10:
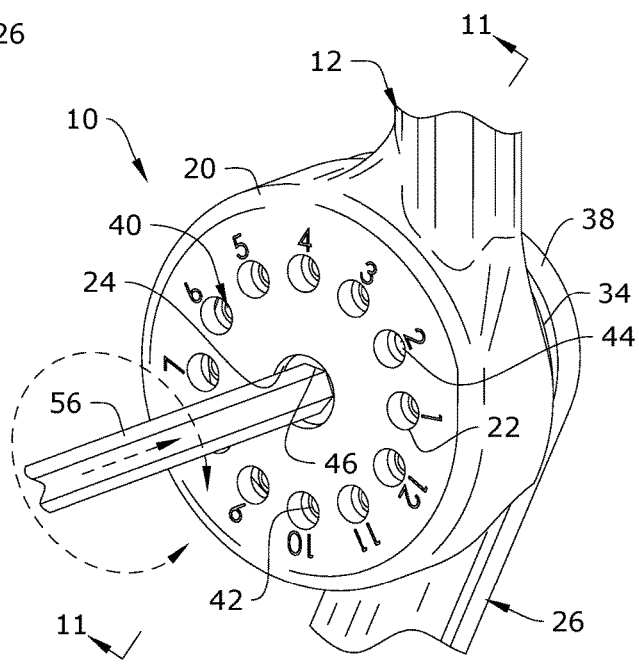
FIG. 10 depicts a perspective view of certain embodiments of the knee brace.
Figure 11:
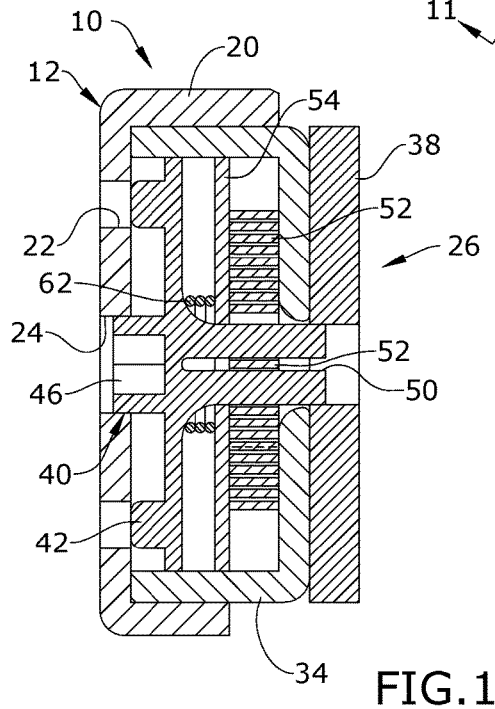
FIG. 11 depicts a section view of certain embodiments of the knee brace taken along line 11-11 in FIG. 10.

FIGS. 10-11 depict knee brace 10 when the torsion setting of the spring assembly is adjusted. Hex tool 56 is inserted into lock plate hex fitting 46 to compress push spring 62. This enables lock plate protrusions 42 and lock plate hex fitting 46 to retract within the interior compartment of upper brace housing 20 and lower brace housing 34. In this retracted state, hex tool 56 is rotated in a first direction such as clockwise to adjust lock plate indicator protrusion 44 to a lower number adjustment setting or a second direction such as counterclockwise to adjust lock plate indicator protrusion 44 to a higher number adjustment setting. Once the desired setting is reached, the user removes hex tool 56 from lock plate hex fitting 46. This causes push spring 62 to extend, which permits lock plate protrusions 42 to extend through lock holes 22 of upper brace housing 20 and lock plate hex fitting 46 to extend through center hole 24 of upper brace housing 20. The current torsion setting of the spring assembly is denoted by the placement of lock plate indicator protrusion 44 in one of the twelve lock holes 22.

As lock plate indicator protrusion 44 is rotated to a higher number adjustment setting, e.g. adjustment setting one to twelve, torsion spring 52 compresses and the amount of mechanical energy stored therein increases. The greater the amount of stored mechanical energy results in a greater resistance of movement of upper brace 12 relative to lower brace 26. This causes knee brace 10 to become more rigid and provides greater weight support capability to operator 58. In contrast, as lock plate indicator protrusion 44 is rotated to a lower number adjustment setting, e.g. adjustment setting seven to one, torsion spring 52 extends and the amount of mechanical energy stored therein decreases. This increases pivotal movement of upper brace 12 relative to lower brace 26 and increases the range of motion of the operator's legs and knees.

The spring assemblies of all knee braces 10 are adjusted in the same manner until torsion requirements of operator 58 are met. Knee brace 10 is advantageous because it permits operator 58 to adjust the spring assemblies as desired to accommodate the support needs of different aged users and users engaging in a variety of activities including, but not limited to, standing, walking, basketball, football, cycling, tennis, motor sports, baseball, other sports, or the like.

It shall be appreciated that the components of knee brace 10 described in several embodiments herein may comprise any alternative known materials in the field and be of any color, size and/or dimensions. It shall be appreciated that the components of knee brace 10 described herein may be manufactured and assembled using any known techniques in the field.

Persons of ordinary skill in the art may appreciate that numerous design configurations may be possible to enjoy the functional benefits of the inventive systems. Thus, given the wide variety of configurations and arrangements of embodiments of the present invention the scope of the invention is reflected by the breadth of the claims below rather than narrowed by the embodiments described above.

What is claimed is:

1. A knee brace configured to be worn by a user with enhanced support and shock absorption capabilities, the knee brace comprising an adjustment mechanism to permit the user to configure the brace with enhanced flexibility to conform to torsion requirements of the user, the knee brace comprising:
   an upper frame assembly configured to detachably couple to the user and comprising a first pair of arms, the first pair of arms coupled together by an upper adjustable strap configured to encircle a thigh portion of the user, each arm in the first pair of arms comprising an upper housing member comprising a wall with a central hole and a plurality of secondary holes disposed along a circular pathway;
   a lower frame assembly configured to detachably couple to the user and comprising a second pair of arms, the second pair of arms coupled together by a lower adjustable strap configured to encircle a leg portion of the user, each arm in the second pair of arms comprising a lower housing member pivotably mounted to one of the upper housing members of the first pair of arms; and
   a pair of spring assemblies operably connected to the upper and lower frame assemblies, each spring assembly in the pair of spring assemblies disposed within one of the upper housing members and one of the lower housing members, and comprising a generally circular lock plate comprising a first face and a second face, the first face comprising a central hex fitting configured to be disposed through the central hole of the upper housing member and a plurality of protrusions configured to be disposed through the plurality of secondary holes in the upper housing member, the second face of the lock plate comprising a support protrusion comprising a central slot, each spring assembly in the pair of spring assemblies comprising a torsion spring with a first end disposed within the central slot of the lock plate and a second end coupled to a torsion spring stop in the lower housing member; wherein the torsion spring is configured to adjust to one of a plurality of positions to store mechanical energy, thereby enabling the upper and lower frame assemblies to provide support to the user according to the torsion requirements.

2. The knee brace of claim 1, wherein each spring assembly further comprises a push spring comprising a first end in contact with the lock plate and a second end in contact with a spring plate, the spring plate comprising an opening configured to permit a portion of the torsion spring to extend therethrough.

3. The knee brace of claim 2, wherein the hex fitting of the lock plate is configured to receive a hex tool to compress the push spring and retract the plurality of protrusions of the lock plate within the upper and lower housing members, thereby permitting the lock plate to rotate in a first direction to compress the torsion spring and increase an amount of mechanical energy stored therein or a second direction to extend the torsion spring to decrease the amount of mechanical energy stored therein.

4. The knee brace of claim 3, wherein the hex tool is configured to be removed from the hex fitting of the lock plate to extend the push spring to permit the plurality of protrusions of the lock plate to extend through the plurality of secondary holes in the upper housing member, thereby maintaining the amount of mechanical energy stored in the torsion spring.

5. The knee brace of claim 4, wherein an interior face of each arm in the first and second pairs of arms comprises a foam plate.

6. The knee brace of claim 5, further comprising an upper arch member coupled to the first pair of arms and a lower arch member coupled to the second pair of arms.

7. The knee brace of claim 6, further comprising a first padding coupled to the upper arch member and a second padding coupled to the lower arch member.

8. The knee brace of claim 7, further comprising a first set of hook and loop fasteners coupled to the upper adjustable strap and a second set of hook and loop fasteners coupled to the lower adjustable strap.

* * * * *